United States Patent

Loux et al.

[11] Patent Number: 5,964,239
[45] Date of Patent: Oct. 12, 1999

[54] HOUSING ASSEMBLY FOR MICROMACHINED FLUID HANDLING STRUCTURE

[75] Inventors: Alan D. Loux, Livermore; William R. Higdon, Pleasanton; Timothy G. Slater, San Francisco, all of Calif.

[73] Assignee: Hewlett-Packard Company, Palo Alto, Calif.

[21] Appl. No.: 08/652,878

[22] Filed: May 23, 1996

[51] Int. Cl.⁶ .............................. F16K 43/00; F16K 27/00
[52] U.S. Cl. ........................... 137/15; 137/315; 137/597; 137/884; 251/11
[58] Field of Search .............................. 137/15, 315, 597, 137/884; 251/11

[56] References Cited

U.S. PATENT DOCUMENTS

| | | | |
|---|---|---|---|
| 3,021,713 | 2/1962 | Wright | 137/597 |
| 3,386,472 | 6/1968 | Szonntagh | 137/597 |
| 4,607,526 | 8/1986 | Bachenheimer et al. | 137/597 |
| 5,069,419 | 12/1991 | Jerman | 251/11 |
| 5,271,597 | 12/1993 | Jerman | 251/11 |
| 5,323,999 | 6/1994 | Boone et al. | 251/11 |
| 5,475,318 | 12/1995 | Marcus et al. | 251/11 |
| 5,640,995 | 6/1997 | Packard et al. | 137/597 |

*Primary Examiner*—George L. Walton
*Attorney, Agent, or Firm*—Skjerven, Morrill MacPherson, Franklin & Friel LLP; Norman R. Klivans

[57] ABSTRACT

A housing for a (silicon) micromachined body (for instance an injector valve system, a detector or a stream selector for a gas chromatograph instrument) is field assemblable and disassemblable and mechanically self-aligning so that the micromachined body may be replaced in the field without tools and without adhesives or permanent bonding. The housing includes a top plate and a bottom plate spaced apart by two side rails and accommodating the micromachined body. The various tubes carrying fluids and pneumatic pressure to and from the micromachined body are attached to the housing by adhesives or brazing or by detachable screw-type fittings. The housing is held in alignment by alignment pins passing through it and is clamped together by a spring clamp which also clamps the housing to a printed circuit board and associated planar heater element. In addition to easy field assembly, this assembly allows manufacturing without precision alignment tools, adhesives, or welding.

17 Claims, 3 Drawing Sheets

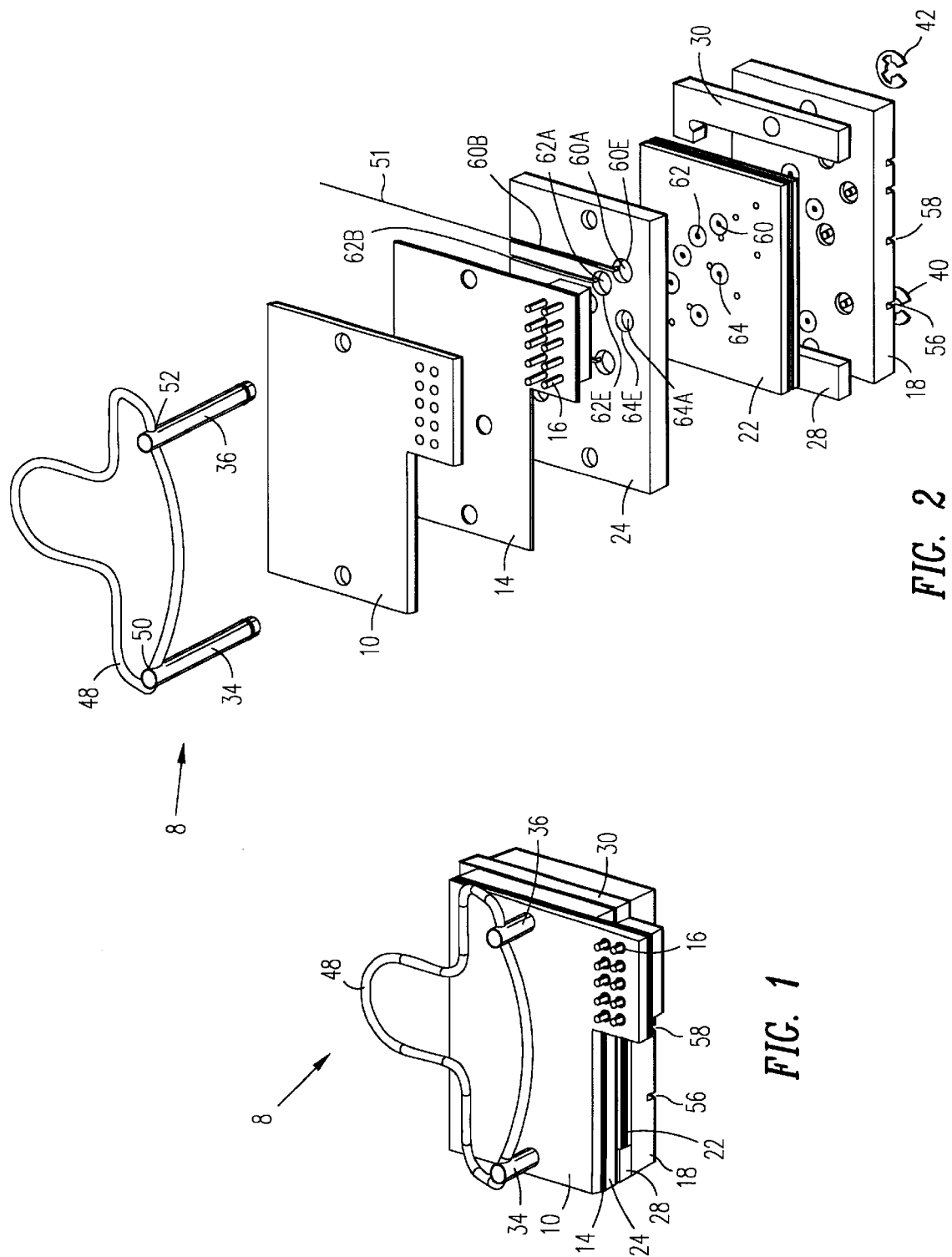

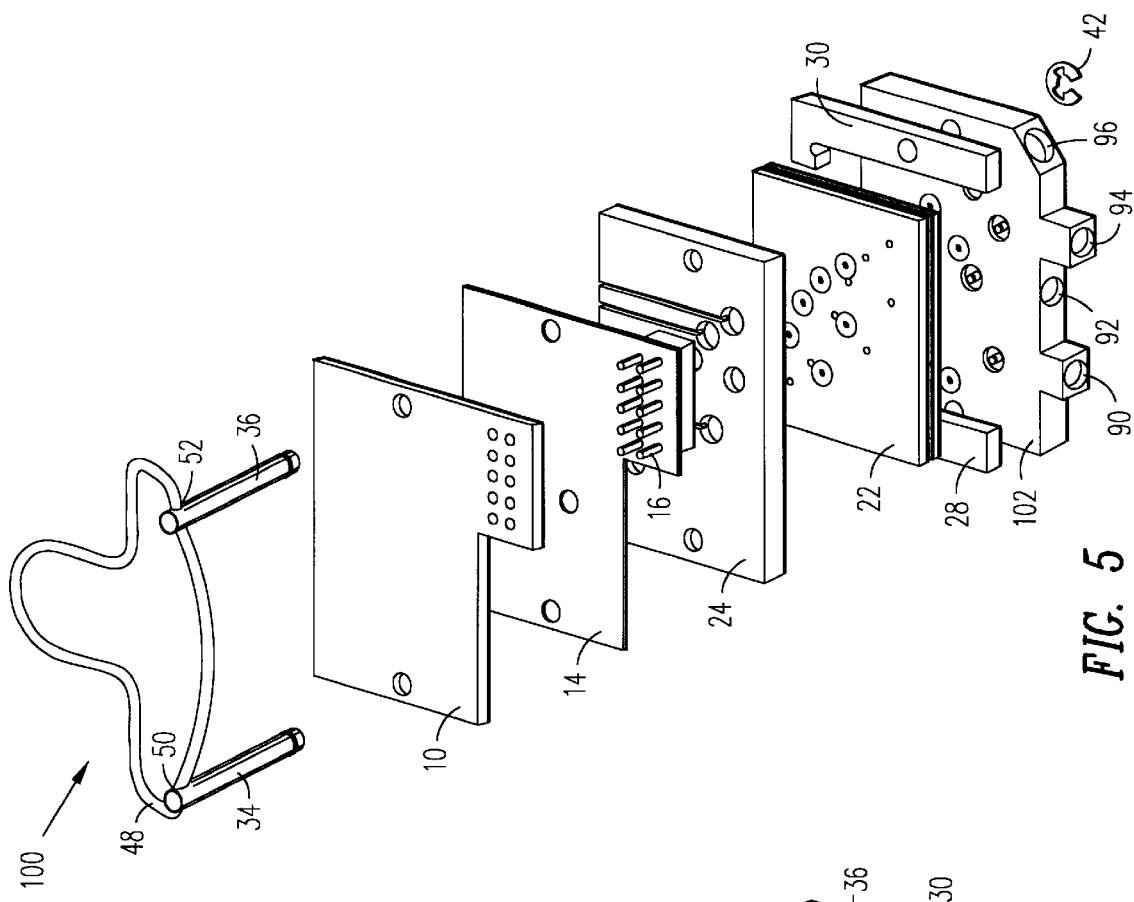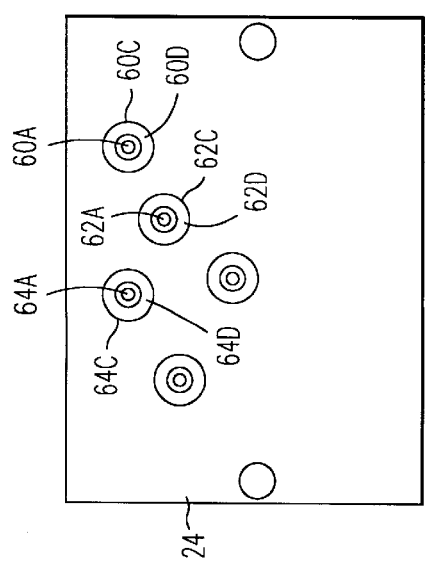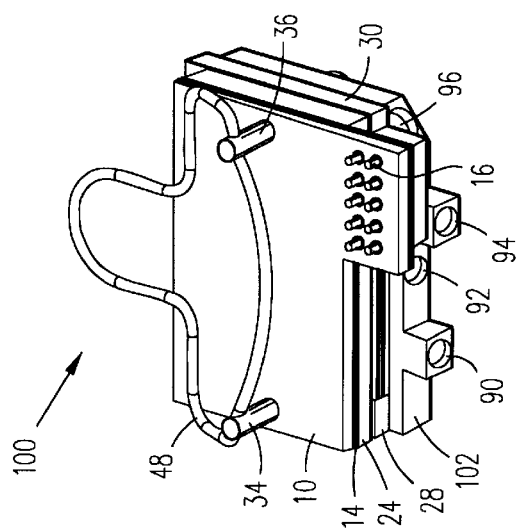

HOUSING ASSEMBLY FOR MICROMACHINED FLUID HANDLING STRUCTURE

BACKGROUND OF THE INVENTION

1. Field of the Invention

This invention relates to micromachined fluid handling structures and more specifically to an easily assembled housing for such a structure.

2. Description of the Prior Art

Micromachined fluid (gas and/or liquid) handling structures are well known. For examples see U.S. Pat. No. 4,471,647 to Jerman et al. and U.S. Pat. No. 4,474,889 to Terry et al., incorporated herein by reference in their entirety, describing respectively a micromachined detector and a fluid valve assembly. These structures (e.g. manifolds, fluid flow and pressure sensors, etc.) include channels and valves which are micromachined by semiconductor-type fabrication techniques typically involving forming structures by photolithography of silicon wafers. The micromachined structure is usually a laminate of several such micromachined layers (including sometimes Pyrex layers or other materials) which are bonded together. In the prior art these micromachined fluid handling structures connect to external components and systems via stainless steel tubes which are permanently bonded to the micromachined structure. The micromachined structure is then permanently encapsulated into a protective body, typically plastic or elastomer. Thus in the prior art this entire assembly is permanently fastened together.

It is not unusual for the micromachined structure to fail, e.g. due to clogs. In this case, the entire assembly is disposed of and replaced with a new one. This is of course expensive. Moreover, not only is the micromachined structure disposed of, also of necessity the connecting tubes which are permanently bonded to the micromachined structure are also thrown away. Therefore replacement of this assembly, in for instance a gas chromatograph instrument, requires factory repair.

Also, initial assembly of such devices in the factory environment is complex, requiring careful alignment and use of suitable adhesives. An additional problem is that many common adhesives are not adequate for high temperature applications.

Thus there is a need for an improved micromachined fluid handling assembly and especially for one which is relatively easy to manufacture and is field replaceable.

SUMMARY

The present inventors have recognized that it would be desirable to provide for an instrument (such as a gas chromatograph) a modularized quick assembly fluid handling apparatus which can be disassembled in the field and into which a new micromachined structure can be readily inserted in the event of failure, without replacing any other components. The user of the instrument thus can perform this task without factory service. This reduces cost of the replacement parts and also makes their replacement easier. In addition, such a modularized assembly allows less expensive assembly even in the factory environment, eliminating the prior art use of adhesives or encapsulation and the requirement for factory alignment fixtures.

In accordance with the present invention, a fluid handling assembly includes a central portion which is a conventional micromachined body, typically a laminate of several micromachined silicon and/or Pyrex layers, which is housed in a modularized easily assembled housing including in one embodiment a top plate, a bottom plate, and two side rails for alignment purposes. Thus no encapsulation or other permanent or semi-permanent assembly techniques are used for housing the micromachined body. The assembly is held together by two alignment pins which each penetrate through the top plate, through one of the side rails, and into the bottom plate. One end of each alignment pin is held by a retainer and the other end is engaged by a spring clamp which compresses the top plate against the bottom plate via the alignment pins, retaining the micromachined body therebetween. Thus the entire assembly is aligned by the alignment pins and is held together by the spring clamp, without any adhesives being used to hold the top plate, bottom plate or side rails to the central micromachined body. Exemplary applications are an injector valve, a detector, or a stream selector, for instance for a gas chromatograph instrument; these applications are illustrative and not limiting.

A seal is made between the top (or bottom) plate to which each tube communicates and the associated ports in the micromachined body in one embodiment by small O-rings located in depressions formed on the inner surface of the plate, the O-rings being in communication with the through holes in the plate. These O-rings in turn each bear around a corresponding port in the outer surface of the micromachined body, each depression thereby being concentric to one internal channel extending to the surface of the micromachined body. Such seals are used for both the fluid carrying channels and the pneumatic channels for valve operation.

Other types of seals may be used. For instance in one version a raised micromachined area on the outer surface of the micromachined body is in contact with a gasket held underneath the corresponding portion of the top plate.

In one embodiment the tubes which carry the fluids and/or pneumatic gases to operate valves in the micromachined body are bonded to, for instance, the top plate and lie in grooves in the outer surface of the top plate, communicating with through holes in the top plate which communicate in turn with associated ports in the micromachined body. Placing the tubes in grooves allows the outer surface of the top plate to be planar so that the clamp can easily bear thereupon. Other types of clamping mechanisms or fasteners may also be used, of the type typically used to hold together small assemblies.

Alternately or in addition, the external tubes are connected to the top and/or bottom plate at the lateral sides of the plate via fittings formed in the plates. These fittings may be of a commercial type which allows a detachable screw-type connection to be made thereto rather than a bonded connection.

Therefore advantageously the micromachined body is easily placed into its quick assembly housing, both for manufacturing and field replacement purposes. The structure of the housing including the alignment pins and other features described herein allows precise alignment of the micromachined body into the housing and to the incorporated tube connections, and also provides seals to prevent leakage of the fluids being carried by the tubes. This eliminates the adhesives and molded structures used in the prior art for such an assembly, which are undesirably costly and prevent field repair or replacement due to their permanence.

BRIEF DESCRIPTION OF THE DRAWINGS

FIG. 1 shows a perspective view of an assembly in accordance with a first embodiment of the present invention.

FIG. 2 shows an exploded view of the structure of FIG. 1.

FIG. 3 shows a plan view of the inner surface of the top plate of FIG. 1.

FIGS. 4 and 5 show respectively a perspective view of an assembly in accordance with a second embodiment of the present invention and an exploded view of the structure of FIG. 4.

DETAILED DESCRIPTION

Figure 6:
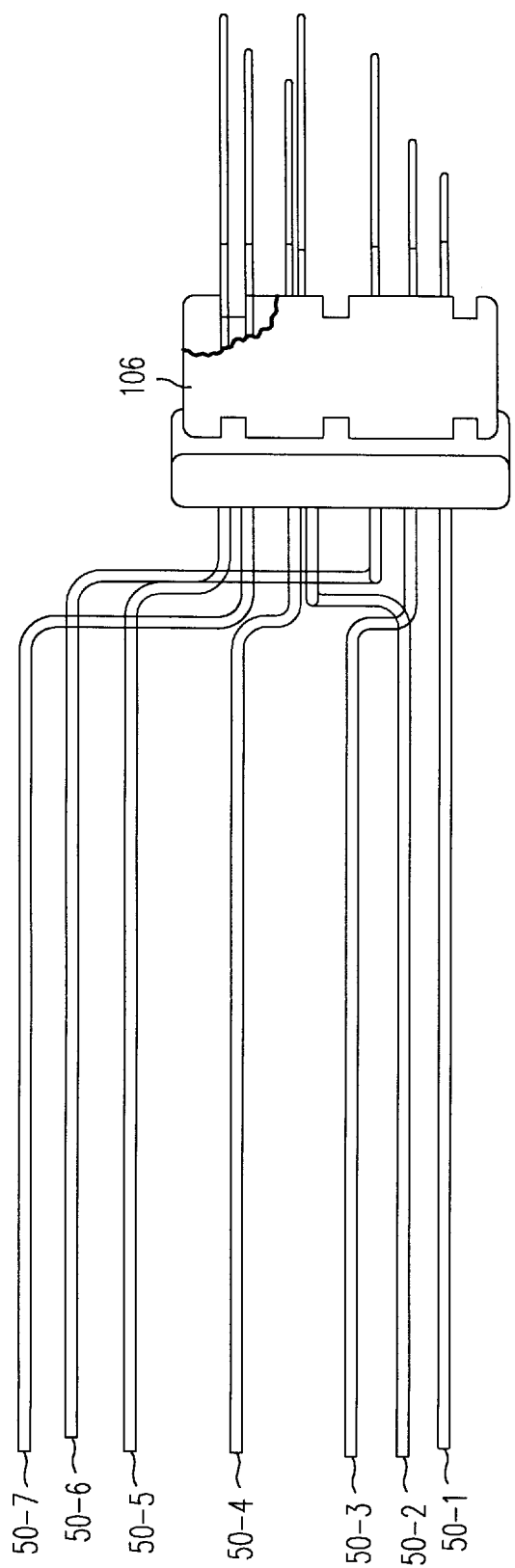
FIGS. 6 and 7 show respectively a plan and side view of the tubes and mounting structure associated with the assemblies of FIGS. 1, 2, 3 and 4.

FIG. 1 shows a perspective view of an assembly 8 in accordance with the present invention. FIG. 2 shows the same structure in an exploded (disassembled) view. The assembly 8 is conventionally mounted in a scientific instrument, e.g. a gas chromatograph, as described below. An (optional) heater 14 is captured between the upper plate 24 and a printed circuit board 10 associated with the heater 14. The heater 14 is a planar device, for instance an insulation layer of Kapton on which are formed resistive heater elements and a heater sensor, and its electrical connector 16 conventionally connects electrically via the PCB 10 to a source of electrical power (not shown) as well as to temperature control circuitry. The purpose of heater 14 is to heat micromachined body 22. The PCB 10 includes the power supply traces and temperature sensors for heater 14, and may include signal processing traces and/or integrated circuitry if for instance body 22 is a detector. The thickness of heater 14 is about 0.010 inch; the width and length of heater 14 corresponds approximately to that of the upper plate 24 with the rectangular extension as illustrated to accommodate connector 16. Alternatively, heater 14 is located between plates 18, 24; in this case the upper plate 24 need not be thermally conductive. In yet another embodiment, heater 14 is merely a set of traces formed directly on a surface micromachined body 22 or inside body 22.

The silicon micromachined body 22 as shown in this embodiment is captured between the lower plate 18 and the upper plate 24 (of course this reference to upper and lower is merely with reference to the drawing; the assembly is operational in various orientations). Body 22 is e.g. a conventional laminated structure as described above and defining a plurality of internal channels, some of which extend to its outer (top and bottom) surfaces. Side rails 28 and 30 space apart the upper plate 24 and lower plate 18 and also retain the silicon body 22 therebetween. The entire assembly is held in alignment by alignment pins 34 and 36 which are for instance stainless steel pins, and which pass entirely through the PCB 10, heater 14, upper plate 24, through respectively side rails 28 and 30, and through the lower plate 18, the ends of the pins 34, 36 protruding from the outer surface of the lower plate 18. In another embodiment, there may be only a single plate (top or bottom) with a clamp securing the micromachined body to the single plate; alternatively the PCB may serve as the second plate.

In this embodiment alignment pins 34 and 36 are retained at their lower ends by E-rings 40, 42 fitting in a slot defined near the end of each of pins 34, 36 as shown in FIG. 2. Other structures are used alternatively to retain the alignment pins; for instance the ends of the alignment pins may be flared out or the pins may be an integral part of the upper or lower plate. In another embodiment, lower plate 18, rails 28, 30, and pins 34, 36 are all formed integrally, e.g. by molding.

Also, in other embodiments there may be only one alignment pin (typically not circular in cross-section in this case) or other alignment structures are used.

The dimensions of this assembly are not critical but are suitable to accommodate a particular micromachined body 22, which for instance is an injector valve assembly, or a detector (which is typically smaller than an injector valve assembly), or a stream selector (manifold) assembly. The actual dimensions of the top plate, bottom plate and side rails are not critical except insofar as they are formed to tolerances to maintain the proper alignment of the micromachined body therebetween. An exemplary thickness of the top plate and bottom plate is each about 0.13 inch, and having a length of 1.3 inch and a width of 0.9 inch.

The spring clamp 48 in one embodiment is a bent loop of e.g. 18 gauge (0.0475 inch diameter) wire which clamps the entire assembly including PCB 10, heater 14, micromachined body 22, and upper and lower plates 24, 18 together. As shown, the spring clamp 48 engages respectively alignment pins 34 and 36 at slanted slots 50 and 52 respectively machined into each of alignment pins 34, 36 near their upper ends. The portion of the spring clamp 48 opposite the curved handle presses on the outer surface of the PCB 10. Pins 34, 36 pass through holes in PCB 10. The pressure exerted by clamp 48 is sufficient to compress the seals between micromachined body 22 and the top and bottom plates 18, 24. Clamp 48 is merely an example of one type of clamp; others may be used. This clamp advantageously is simple to manufacture and to use because it does not require any tools to engage or disengage, thus allowing easy field assembly and disassembly as well as easy factory assembly.

Also shown in FIG. 2 is one exemplary fluid carrying tube 50 extending into the upper surface of upper plate 24. Tube 50 carries pneumatic pressure or fluids into/out of micromachined body 22 as explained below. Other fluid carrying tubes (not shown for clarity) also connect to upper plate 24. Further such tubes connect into the front lateral surface of lower plate 18 as described further below e.g. lying in grooves 56, 58. It is to be understood that the number and location of the fluid carrying tubes conventionally is determined by the particular functionality of micromachined body 22.

FIG. 2 illustrates the upper surface of micromachined body 22, i.e. that which is in contact with the lower surface of the upper plate 24. Labelled are three exemplary ports 60, 62 and 64 each communicating with associated channels (not visible) formed inside the micromachined body structure 22. Ports 60, 62, 64 may be fluid ports or valve actuation ports. A micromachined body may have more ports and more channels including several valves of the type described in e.g. U.S. Pat. No. 5,487,313 to Paul H. Johnson, incorporated herein by reference in its entirety.

For each port 60, 62 and 64 there is a corresponding through hole 60A, 62A and 64A (e.g. 0.030 inch in diameter) in the upper plate 24 as also illustrated in FIG. 2. These through holes in upper plate 24, when the entire assembly is assembled, fit exactly over the corresponding ports 60, 62, 64 in the micromachined body 22 for passage of fluids. Surrounding each of through holes 60A, 62A and 64A in the upper surface of upper plate 24 is a corresponding recess 60E, 62E and 64E which is not a through hole and is e.g. 0.125 inch in diameter. Each depression 60E, 62E and 64E communicates with a groove respectively 60B, 62B and 64B which extends from the associated depression to the rear edge of upper plate 24. The grooves are e.g. 0.030 inch wide.

Thus a tube 50, which is a narrow diameter (0.029 inch) stainless steel tube, lies in each of grooves 60B, 62B and 64B and extends down into the through holes respectively 60A, 62A and 64A. (It is to be understood that FIG. 2 shows only one tube 50, for purposes of illustration.) Each stainless steel tube is retained in its respective groove and depression by, e.g. epoxy adhesive or brazing. Thus these tubes communicate with the interior channels (not visible) in the silicon body 22. By providing each tube with a 90° bend at the point it exits the associated depressions 60A, 62A and 64A, and placing each tube in a groove, the outer surface of the upper plate 24 is thereby planarized to provide a planar surface for heater 14 to lie upon. In other embodiments with other types of clamping arrangements the stainless steel tubes need not be planarized in the upper plate 24 but instead may extend orthogonal outwardly. A typical depth of depressions 60E, 62E, 64E is 0.08 inch. This and other dimensions herein are illustrative and not limiting.

The lower surface of upper plate 24 (not visible in FIG. 2) is illustrated in a plan view in FIG. 3. Labelled are through holes respectively 60A, 62A and 64A, surrounded respectively by a concentric depression (recess) 60C, 62C and 64C, each depression being e.g. 0.104" in diameter and having a depth of e.g. 0.030". Captured in each depression 60C, 62C and 64C is a small flexible (Viton) O-ring which acts as a seal to a corresponding portion silicon body 22 and around the associated tube. Thus the depth of recesses 60C, 62C, 64C is determined by the thickness of the O-ring so that a portion of the O-ring protrudes above the plane of the inner surface of plate 24. These O-rings are shown as structures 60D, 62D and 64D. In one embodiment these are very small O-rings of commercially available type which seal against body 22; a typical alignment tolerance for each O-ring is ±0.005 inch, for an O-ring having an (uncompressed) inside diameter of 0.029 inches.

It is to be understood that this particular O-ring sealing structure is illustrative and not limiting. The need is for a seal which is relatively easy to align and yet which is not permanently bonded, because the assembly 8 is to be easily disassembled with the upper plate 24 being easily separated from the micromachined body 22.

Other types of seals may be used. An example is a raised circular glass area formed (etched) surrounding each port of the micromachined body 22. The raised glass area engages a corresponding elastic sheet gasket, for instance of Kapton, captured between plate 24 and micromachined body 22 with small diameter holes provided at appropriate locations in the sheet gasket corresponding to ports 60, 62, and 64.

Another type of seal, which does not require an organic material such as Viton or Kapton, is a soft metal (e.g. gold) seal located appropriately around each port. Such gold (or other soft metal) seals are e.g. deposited or plated or sputtered onto the inner surface of upper plate 24 (or could be small washers) and bear against opposing valve seals or seal seats formed in the upper surface of silicon body 22. Some seals are more temperature resistant than others. For instance a Kapton gasket seal would be operable up to 220° C. whereas a metal seal would be operable at higher temperatures. Also the Kapton gasket-raised glass seal or the metal seal are suitable for very small diameter ports which may be too small or too close together for use of commercially available O-rings. Other types of fluid seals may also be used.

As understood from FIGS. 1 and 2, assembly (either initially in the factory or later in the field) is quite simple. When assembly 8 has been assembled and it is desired to disassemble it in the field and reassemble it with a new micromachined body, for instance due to a failure of the old micromachined body, one merely releases the spring clamp 48 by pushing its handle up and removing it from its position in the slots in the alignment pins 34 and 36. It is then easy to pull the upper plate 24 vertically away from the micromachined body 22 and extract the micromachined body 22 by moving it horizontally to slide out between the side rails 28 and 30. The micromachined body then is discarded and replaced by a new one. The new micromachined body is slid between the rails 28 and 30. Rails 28 and 30 pivot about respective alignment pins 34 and 36 as the micromachined body is inserted between rails 28 and 30. In one embodiment (not illustrated) the inner surfaces of rails 28 and 30 are formed at their outer ends (the ends shown in FIG. 1) to define a lead-in for easy insertion of micromachined body 22.

As shown, each of rails 28 and 30 (see FIG. 2) is L-shaped, providing a back surface to which to align the micromachined body 22 so that micromachined body 22 is perfectly aligned within the assembly consisting of lower plate 18, upper plate 24 and side rails 28 and 30. The sides of micromachined body 22 rest against the side rails 28 and 30 which provide the desired precision alignment. The side rails 28 and 30 are held in position by the alignment pins 34 and 36.

In another embodiment, side rails 28 and 30 are an integral part of either the top plate 24 or the bottom plate 18 and not independent structures. However making side rails 28, 30 separate structures is easier to fabricate (machine or mold) and also provides the above-described capability for the side rails to pivot for easier insertion of body 22.

As seen in FIG. 1, clamp 48 provides three point pinching against assembly 8 so that clamp 48 pulls up on the two alignment pins 34 and 36 which are held by their retainers 40, 42 against the lower plate 18. In one embodiment where heater 14 is not present, instead a spacer of the same thickness as heater 14 is provided so the assembly clamps together snugly with the same clamp 48.

Suitable materials for the bottom plate 18, top plate 24 and side rails 28 and 30 are machined or sintered (molded) stainless steel or aluminum. At least top plate 24 is thermally conductive in the case where a heater 14 is on its outer surface. Otherwise these structures need not be metal but may be other materials which of requisite strength and rigidity for precision alignment purposes.

This particular alignment arrangement is illustrative and not limiting. In another version the micromachined body 22 defines rectangular cutouts in its side surface which terminate at pins 34, 36, so that the cutouts align directly against alignment pins 34 and 36, in this case without use of the side rails 28 and 30. This of course requires more extensive fabrication in terms of forming the sides surfaces of silicon body 22.

In FIG. 2 fluid carrying tubes, e.g. tube 50 and others not shown, extend into the through holes at the upper surface of upper plate 24. However in one embodiment alternative or additional grooves 56, 58 for additional fluid carrying tubes are defined extending to the front or rear side surfaces of lower plate 18 (or upper plate 24) as shown in FIG. 1. Tubes lying in grooves 56, 58 are used e.g. in the gas chromatograph instrument injector valve application to carry fluid to/from the instrument column. It is to be understood that the tubes lying in e.g. grooves 56, 58 are in communication with through holes in lower plate 18 as illustrated, which seal in turn against corresponding ports in the lower surface (not shown) of micromachined body 22, as described above with reference to the upper surface of micromachined body 22.

In another embodiment as shown in FIG. 4 and in FIG. 5 which is an exploded view of assembly 100 of FIG. 4, additional fluid carrying tubes are connected to the assembly 100 by means of ferrule-nut type connectors of the type commercially available from Valco Instruments Company, Inc. Assembly 100 of FIGS. 4 and 5 is in most respects identical to that of FIGS. 1 and 2, and similar structures have identical reference numbers. The difference is that instead of tube grooves 56, 58 in FIGS. 1 and 2, in FIGS. 4 and 5 the fluid carrying tube connections in lower plate 102 differ. These tube connections use a threaded ferrule cone-shaped (male) stainless steel connector (not shown) on the end of each tube which threads into a corresponding female connector formed in lower plate 18, instead of using a welded/bonded tube connection. Advantageously these threaded connectors are readily disconnectable by unscrewing their nuts which are a part of the male connector (not shown) from the corresponding conical threaded female connectors 90, 92, 94, 96 which in this embodiment are machined into the side surfaces of lower plate 18. These female connectors 90, ..., 96 connect to internal channels (not shown) defined in lower plate 18 which in turn communicate via seals, of the type described above, to the ports formed in the lower surface of micromachined body 22.

It is to be understood that use of the threaded fittings or tube-and-groove approach is a matter of convenience; either or both (or other tube attachment techniques) can be used.

These commercial-type threaded fittings have a characteristic internal conical shape for the female portion. In one embodiment a filter (not shown) is located in the apex of at least one of the cones inside lower plate 18, e.g. to filter incoming fluids to remove particulates. For instance this filter is a body of stainless steel frit packed into the cone apex. Advantageously the filter is extremely close to the point of use of the fluid in the micromachined body 22. For instance if the micromachined body 22 is a gas chromatograph detector, the filter is within 0.1 inch of the actual detector, thus making sure that the filter is at its optimum position. This is a significant improvement over prior art in-line filters which typically are located in the external tubing.

Figure 7:
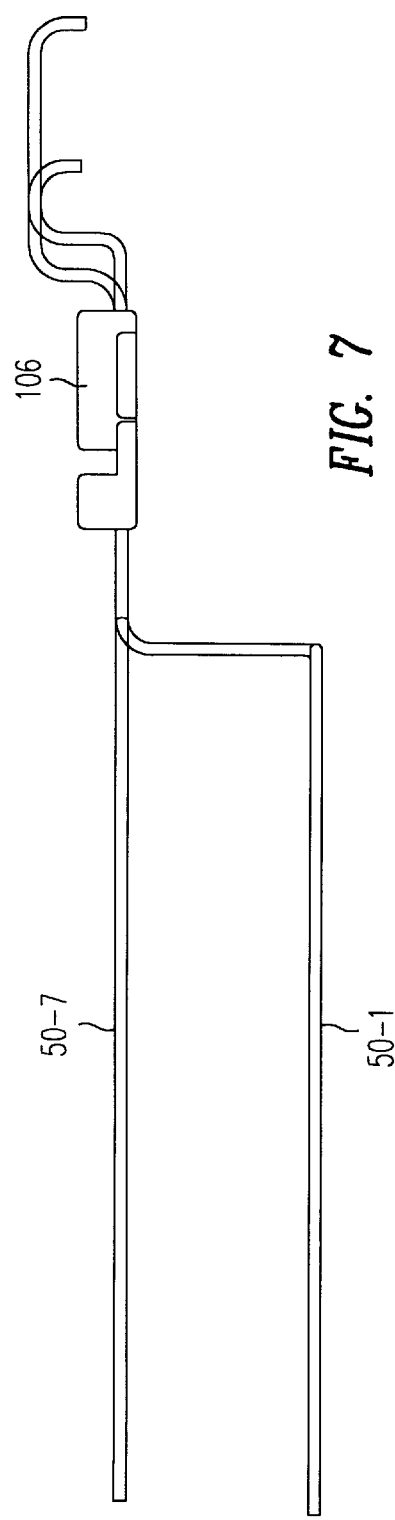

FIGS. 6 and 7 show one approach to mounting an assembly as described above in an instrument. The tubes 50-1, 50-2, 50-3, ..., 50-7 connecting into the assembly 8 (or assembly 100) are bonded into the grooves of top plate 24, and extend away from assembly 8. (In FIGS. 6 and 7, the ends of the tubes to the right side of the drawing connect to assembly 8.) Each tube is secured into and passes through an e.g. plastic mounting member 106, which in turn is secured into the instrument (not shown) by sliding the mounting member 106 into a slot in e.g. a sheetmetal chassis of the instrument.

This disclosure is illustrative and not limiting; further modifications will be apparent to one skilled in the art in light of this disclosure and are intended to fall within the scope of the appended claims.

We claim:

1. A fluid handling assembly comprising:
   a micromachined body having two principal surfaces and defining a plurality of internal channels for passage of fluid, each internal channel being in communication with at least one principal surface of the body and being in communication with an associated pneumatically operated valve formed in the body;
   at least a first plate in direct contact with a first of the principal surfaces, wherein the first plate defines a plurality of through holes each juxtaposed to one of the internal channels at the principal surface of the micromachined body which is in direct contact with the first plate, each through hole supplying pneumatic fluid to actuate the associated valve;
   an alignment structure in contact with the first plate and the micromachined body; and
   a clamping mechanism exerting pressure on the first plate and the micromachined body, thereby to hold the first plate to the micromachined body.

2. The assembly of claim 1, further comprising:
   a second plate in contact with a second of the principal surfaces of the micromachined body; wherein the alignment structure includes at least one alignment member extending from the first plate to the second plate and at least a first rail spacing apart the first and second plates and being in contact with a first lateral surface of the micromachined body.

3. The assembly of claim 2, wherein the alignment structure further comprises a second rail spacing apart the first and second plates and being in contact with a second opposing lateral surface of the micromachined body.

4. The assembly of claim 3, wherein the one alignment member passes through one of the first and second rails.

5. The assembly of claim 3, wherein the clamping mechanism includes a clamp held in a slot in an end portion of the alignment member protruding from the first plate.

6. The assembly of claim 3, an end of the alignment member protruding through the second plate and being retained by a retainer near the protruding end of the alignment member.

7. The assembly of claim 1, further comprising a planar substrate in contact with a planar surface of the first plate.

8. The assembly of claim 1, further comprising a planar heater element in thermal contact with the first plate.

9. The assembly of claim 1, further comprising a plurality of tubes, one tube being in communication with each of the plurality of through holes, each tube lying in a groove defined in an outer surface of the first plate.

10. The assembly of claim 1, each through hole defining on an interior surface of the first plate a depression concentric to the through hole, there being a seal located in the depression.

11. The assembly of claim 1, each internal channel at the principal surface of the micromachined body terminating in a seal protruding from the principal surface, there being a flexible structure lying between each seal and the adjacent surface of the first plate which is in contact with the principal surface of the micromachined body.

12. The assembly of claim 1, the first plate defining a plurality of internal channels extending to a side surface of the first plate and each of the plurality of internal channels in the first plate terminating at the side surface of the first plate at a threaded conical cavity, adapted for threaded attachment to an exterior corresponding threaded fitting.

13. The assembly of claim 12, further comprising a filter body located at an apex of at least one of the threaded conical cavities.

14. A method of assembling a structure including a micromachined body defining a plurality of internal channels for passage of a fluid, the internal channels each being in communication with at least one surface of the micromachined body, the method comprising the steps of:
   placing the micromachined body in contact with a plate structure;
   aligning the micromachined body with the plate structure using non-threaded alignment pins extending through the micromachined body into the plate structure;

clamping together the plate structure and the micromachined body using a spring clamp engaging an exposed end of the alignment pins and exerting pressure on the plate structure, thereby not requiring any tools to engage or disengage the spring clamp; and threadably attaching fluid carrying tubes to be in communication with the internal channels in the micromachined body.

15. The method of claim 14, wherein the step of threadably attaching comprises the step of screwing the tubes into corresponding threaded fittings in one of the plates.

16. The method of claim 14, further comprising the step of sealing each of the internal channels where it extends to a principal surface of the micromachined body to corresponding through holes in the plate structure.

17. The method of claim 14, wherein the step of placing includes placing the micromachined body in contact with a second plate structure, and the step of clamping includes clamping the micromachined structure between the two plate structures.

* * * * *